United States Patent [19]

Mixson et al.

[11] Patent Number: Plant 6,921

[45] Date of Patent: Jul. 11, 1989

[54] ST. AUGUSTINE GRASS '6-72-182'

[75] Inventors: Wayne C. Mixson, Apopka, Fla.; Terrance P. Riordan, Lincoln, Nebr.; Virgil D. Meier, Marysville, Ohio

[73] Assignee: The O. M. Scott & Sons Company, Marysville, Ohio

[21] Appl. No.: 185,523

[22] Filed: Apr. 25, 1988

[51] Int. Cl.[4] ..... A01H 5/00

[52] U.S. Cl. ..... Plt./88

[58] Field of Search ..... Plt./88

*Primary Examiner*—James R. Feyrer

[57] ABSTRACT

A perennial St. Augustine grass with yellow anthers and white stigmas having very good turf performance, good cold tolerance, short internodes and leaves and good resistance to gray leaf spot.

1 Drawing Sheet

BACKGROUND

A St. Augustine grass which has been named "Seville" was disclosed in U.S. Plant Pat. No. 4,097, which issued on Sept. 6, 1977. Another St. Augustine grass which has been named "Delmar" was disclosed in U.S. Plant Pat. application Ser. No. 893,960, filed Aug. 7, 1986. A further St. Augustine grass designated 6-72-130 is disclosed in U.S. Plant Pat. application Ser. No. 07/185,524, filed or even date herewith.

SUMMARY OF THE VARIETY

The present invention relates to a new and distinct perennial St. Augustine grass selected from the progeny of a controlled pollination of a cold tolerant selection obtained from Memphis, Tenn. with the pollen of Seville. This yellow anther, white stigma genotype was labeled 6-72-182 and propagated vegetatively by stolons to provide planting stock for studying performance and making comparisons to present commercial varieties.

The combination of yellow anthers, white stigma, short and thin internodes, short leaf blades, good cold tolerance, a low tendency for purple stems, good resistance to gray leaf spot and very good turf quality of 6-72-182 along with other information allow this genotype to be distinguished from other St. Augustine grasses.

DETAILED DESCRIPTION OF THE VARIETY

Figure 1:
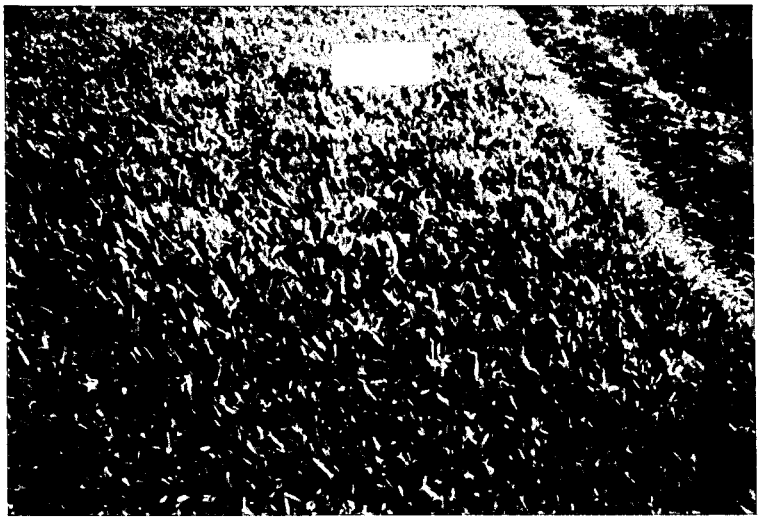
FIG. 1 is a photograph of 6-72-182 St. Augustine turf.
Figure 2:
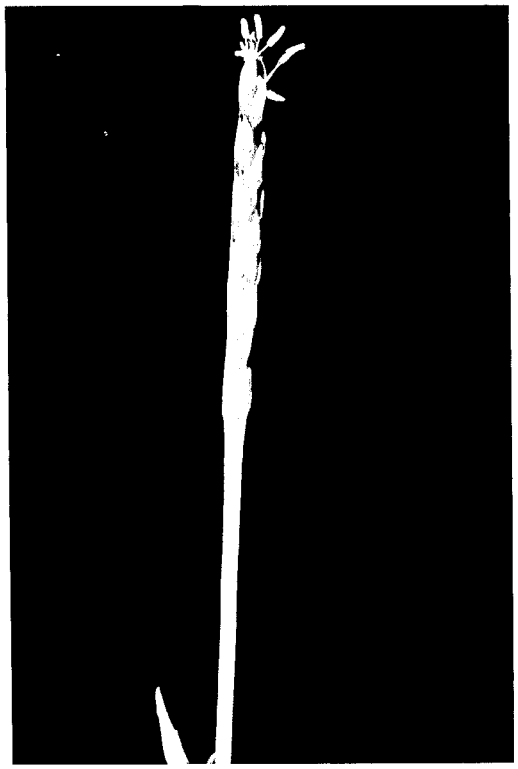
FIG. 2 shows a single spike of a 6-72-182 St. Augustine grass plant depicting yellow anthers and white stigmas protruding from several spikelets.
Figure 3:
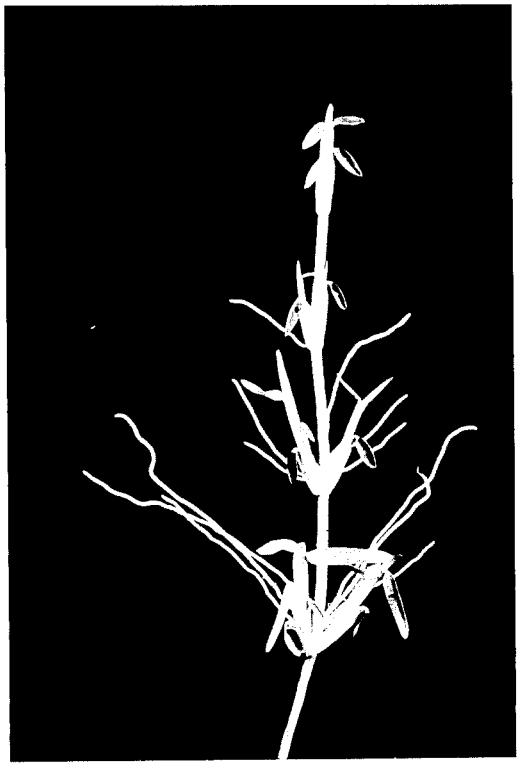
FIG. 3 is a photograph of a vegetative stolon of 6-72-182 St. Augustine grass.

Genotype 6-72-182 has a yellow anther color, a white stigma color, and an unreduced chromosome number of 18. The internodes and leaf blades are shorter than most other St. Augustine varieties. The combination of shorter internodes and leaf blades along with narrower than average leaf blades results in a turf that is generally more dense, finer textured and produces fewer clippings when mowed. Measurements of the spike and related structures indicate that 6-72-182 has a shorter and narrower spike, a peduncle that is shorter than average and thinner than most varieties, a shorter and narrower flag leaf and a shorter flag leaf sheath than most varieties of St. Augustine grass. The chromosome numbers, anther and stigma color and morphological measurements of 6-72-182 and other St. Augustine grasses are compared in Tables 1–4.

TABLE 1

Chromosome numbers, anther color, and stigma color of 6-72-182 and other St. Augustine grasses

| Selection/Variety | Chromosome Number | Anther Color | Stigma Color |
|---|---|---|---|
| 6-72-182 | 18 | Yellow | White |
| 6-72-130 | 18 | Purple | Purple |
| Bitterblue | 27 | Yellow | Purple |
| Delmar | 18 | Yellow | White |
| Floratam | 27 | Yellow | Purple |
| Floratine | 27 | Yellow | Purple |
| Raleigh | 18 | Yellow | White |
| Seville | 18 | Yellow | Purple |
| Texas Common | 18 | Yellow | White |
| California Common | 18 | Yellow | White |
| 1081 | 18 | Purple | Purple |

TABLE 2

Comparative measurements of internode length and thickness of 6-72-182 and other St. Augustine grasses.

| | Internode[a] | | | |
|---|---|---|---|---|
| | | Diameter (mm)[b] | | |
| Selection/Variety | Length (cm) | Longest | Shortest | Flat[c] |
| 6-72-182 | 4.8 | 2.8 | 2.2 | 1.32 |
| 6-72-130 | 5.6 | 2.7 | 1.9 | 1.44 |
| Bitterblue | 6.9 | 2.7 | 2.1 | 1.30 |
| Delmar | 5.7 | 3.5 | 2.6 | 1.35 |
| Floratam | 7.5 | 3.2 | 2.5 | 1.25 |
| Floratine | 5.8 | 2.7 | 2.2 | 1.30 |
| Raleigh | 7.0 | 3.2 | 2.5 | 1.27 |
| Seville | 6.8 | 2.7 | 2.2 | 1.25 |
| Texas Common | 6.2 | 3.0 | 2.2 | 1.35 |
| California Common | 4.2 | 2.4 | 2.0 | 1.22 |
| 1081 | 7.3 | 2.8 | 2.0 | 1.38 |
| LSD (.05) | 1.15 | 0.24 | 0.27 | 0.091 |

[a]Greenhouse planting at Marysville, Ohio. Measurements taken on unclipped potted plants using third internode from terminal end of stolon.

[b]Diameter measurements taken at the approximate center of the internode which has an elliptical shaped cross section.

[c]Flatness index equals longest axis divided by shortest axis. A larger flatness index indicates a flatter shaped stem.

TABLE 3

Comparative Leaf Blade Length, Width and Sheath Length of 6-72-182 and other St. Augustine grasses[a].

| | Blade Length (cm) | | Blade | Sheath |
|---|---|---|---|---|
| Selection/Variety | High[b] Light | Low[c] Light | Width[b] (cm) | Length[b] (cm) |
| 6-72-182 | 5.3 | 13.7 | 1.5 | 2.3 |

TABLE 3-continued

Comparative Leaf Blade Length, Width and Sheath Length of 6-72-182 and other St. Augustine grasses[a].

| Selection/Variety | Blade Length (cm) High[b] Light | Blade Length (cm) Low[c] Light | Blade Width[b] (cm) | Sheath Length[b] (cm) |
|---|---|---|---|---|
| 6-72-130 | 5.2 | 14.8 | 1.3 | 2.7 |
| Delmar | 7.3 | 16.7 | 1.8 | 3.3 |
| Bitterblue | 7.4 | 17.5 | 1.5 | 2.8 |
| Floratam | 10.1 | 27.2 | 1.7 | 4.5 |
| Floratine | 8.6 | 16.3 | 1.4 | 3.2 |
| Raleigh | 7.8 | 13.8 | 1.7 | 3.7 |
| Seville | 6.9 | 18.4 | 1.4 | 2.9 |
| Texas Common | 8.1 | 16.6 | 1.7 | 3.6 |
| California Common | 3.8 | 11.8 | 1.2 | 2.2 |
| 1081 | 7.8 | 15.2 | 1.5 | 3.2 |
| LSD (.05) | 2.03 | 3.25 | 0.17 | 0.71 |

[a]Greenhouse Planting - Marysville, Ohio. Measurements taken on unclipped potted plants.
[b]After a period of natural sunlight and a high level supplemental light.
[c]After a lengthy period of very cloudy conditions and no supplemental light.

TABLE 4

Comparative measurements of the inflorescence and related structures of 6-72-182 and other St. Augustine grasses[a].

| Selection/Variety | Spike Length (mm) | Spike Width (mm) | Peduncle Length (mm) | Peduncle Width (mm) |
|---|---|---|---|---|
| 6-72-182 | 60 | 4.3 | 52 | 1.6 |
| 6-72-130 | 56 | 4.8 | 41 | 1.7 |
| Delmar | 93 | 5.3 | 68 | 2.1 |
| Bitterblue | 78 | 5.6 | 61 | 2.2 |
| Floratam | 96 | 5.9 | 83 | 2.4 |
| Floratine | 74 | 5.8 | 48 | 2.3 |
| Raleigh | 72 | 5.8 | 62 | 2.2 |
| Seville | 71 | 4.9 | 50 | 1.9 |
| Texas Common | 68 | 4.9 | 42 | 1.9 |
| 1081 | 78 | 5.2 | 60 | 1.9 |
| LSD (.05) | 10.0 | .64 | 18.3 | 0.28 |

| Selection/Variety (mm) | Flag Leaf Length (mm) | Flag Leaf Sheath Width (mm) |
|---|---|---|
| 6-72-182 | 16 | 6.0 |
| 6-72-130 | 30 | 5.9 |
| Delmar | 21 | 6.7 |
| Bitterblue | 22 | 6.4 |
| Floratam | 35 | 6.3 |
| Floratine | 27 | 7.2 |
| Raleigh | 25 | 7.5 |
| Seville | 15 | 5.8 |
| Texas Common | 29 | 7.1 |
| 1081 | 25 | 6.3 |
| LSD (.05) | 12.4 | 1.08 |

[a]Greenhouse planting - Marysville, Ohio.

Field observations of 6-72-182 indicate that it has very good turf quality characteristics throughout the year and across the area of the United States where St. Augustine grass is adapted. It performs especially well in the Florida climate. Although it performs best during the hotter summer months, it has good cold tolerance and performs better during the winter months than most readily available commercial varieties. These characteristics of 6-72-182 as compared with other St. Augustine grasses for turf quality and cold injury are illustrated in Tables 5–7.

TABLE 5

Comparative turf quality[a] of 6-72-182 and other St. Augustine grass varieties at Apopka, Florida.

| Selection/Variety | Summer | Winter | Mean |
|---|---|---|---|
| 6-72-182 | 9.3 | 8.3 | 8.7 |
| 6-72-130 | 8.2 | 7.6 | 7.8 |
| Bitterblue | 7.3 | 5.9 | 6.0 |

TABLE 5-continued

Comparative turf quality[a] of 6-72-182 and other St. Augustine grass varieties at Apopka, Florida.

| Selection/Variety | Summer | Winter | Mean |
|---|---|---|---|
| Delmar | 9.8 | 9.0 | 9.6 |
| Floratam | 7.5 | 5.8 | 6.1 |
| Floratine | 7.2 | 6.1 | 6.4 |
| Florida Common | 8.2 | 6.6 | 7.0 |
| Raleigh | 6.7 | 7.1 | 7.4 |
| Seville | 9.0 | 7.9 | 8.1 |
| Texas Common | 6.5 | 8.4 | 8.0 |
| 1081 | 8.7 | 6.8 | 7.3 |
| LSD (.05) | 0.45 | 0.99 | 0.88 |

[a]Quality-rated 1–10, 10 = best.

TABLE 6

Comparative turf quality[a] of 6-72-182 and other St. Augustine-grass varieties at the South Coast Field Station of the University of California - Riverside.

| Selection/Variety | Turf Quality Summer | Turf Quality Winter | Turf Quality Mean |
|---|---|---|---|
| 6-72-182 | 5.8 | 4.5 | 5.0 |
| 6-72-130 | 6.6 | 4.6 | 5.4 |
| Calif. Common | 5.4 | 4.2 | 4.7 |
| Delmar | 5.3 | 4.7 | 4.9 |
| Floratam | 5.4 | 4.1 | 4.6 |
| Raleigh | 4.6 | 3.3 | 3.9 |
| Texas Common | 5.5 | 4.3 | 4.8 |
| LSD (.05) | 0.50 | 0.44 | 0.39 |

[a]Quality-rated 1–10, 10 = best.

TABLE 7

Comparative cold injury of 6-72-182 and other St. Augustine grasses in Apopka, Florida

| Selection/Variety | Cold Injury (%) Expt. 1 | Expt. 2 | Expt. 3 | Expt. 4 | Mean |
|---|---|---|---|---|---|
| 6-72-182 | 21 | 5 | 35 | 28 | 22 |
| 6-72-130 | 35 | 17 | 38 | 18 | 27 |
| Bitterblue | 53 | 38 | 58 | 34 | 46 |
| Delmar | 0 | 0 | 17 | 3 | 5 |
| Floratam | 40 | 42 | 55 | 40 | 44 |
| Floratine | 48 | 32 | 37 | 26 | 36 |
| Raleigh | 32 | 12 | 37 | 13 | 23 |
| Seville | 35 | 15 | 37 | 24 | 28 |
| Texas Common | 18 | 7 | 33 | 28 | 21 |
| 1081 | 47 | 33 | 48 | 33 | 40 |
| LSD (.05) | 20.9 | 18.5 | 26.1 | 23.5 | 16.5 |

Color of turf is an important component of turf quality. 6-72-182 has a good dark green color during the summer months which is darker green than most St. Augustine varieties, and during the winter months its color is comparable to other varieties. Other factors that have shown varietal differences include: tendency to turn brown during the winter, for which 6-72-182 is rated about average; susceptibility to Asulox (an important herbicide) to which 6-72-182 is not susceptible; purple stem color, especially during cold weather, for which 6-72-182 has a very low tendency; susceptibility to gray leaf spot to which 6-72-182 has good resistance; and susceptibility to chinch bugs to which 6-72-182 has shown no greater susceptibility than most other varieties. Data on turf color, winter browning, Asulox injury, purple stems, gray leaf spot and chinch bugs are in illustrated in Tables 8–12.

TABLE 8

Comparative color ratings of 6-72-182 and other St. Augustine grass at various locations in the U.S.

| Selection/Variety | Color[a] Florida[b] Summer | Mean | California[c] |
|---|---|---|---|
| 6-72-182 | 9.8 | 8.5 | 3.9 |
| 6-72-130 | 8.6 | 7.7 | 3.8 |
| Bitterblue | 8.5 | 7.6 | — |
| Calif. Common | — | — | 3.8 |
| Delmar | 10.0 | 8.9 | 4.6 |
| Floratam | 8.8 | 7.8 | 4.2 |
| Floratine | 8.0 | 7.5 | — |
| Florida Common | 8.3 | 7.9 | — |
| Raleigh | 7.0 | 6.5 | 3.4 |
| Seville | 9.2 | 8.5 | — |
| Texas Common | 6.8 | 7.9 | 4.0 |
| 1081 | 8.8 | 8.0 | — |
| LSD (.05) | 0.48 | 0.67 | 0.35 |

[a]Color rated 1-10, 10 = darkest green
[b]Test planted at Apopka, Florida
[c]Test planted at South Coast Field Station, University of California - Riverside.

TABLE 9

Comparative ratings of various attributes of 6-72-182 and other St. Augustine grasses which detract from overall appearance.

| Selection/Variety | Brown[a] | Asulox[b] |
|---|---|---|
| 6-72-182 | 5.0 | 0 |
| 6-72-130 | 6.3 | 5 |
| Delmar | 3.7 | 0 |
| Bitterblue | — | 12 |
| Floratam | 6.3 | 0 |
| Floratine | — | 2 |
| Raleigh | 8.3 | 10 |
| Seville | — | 3 |
| Texas Common | 5.7 | 0 |
| California Common | 4.0 | — |
| 1081 | — | 7 |
| LSD (.05) | 2.0 | 5.3 |

[a]Test planted at South Coast Field Station - University of California - Rated as % brown turf.
[b]Test planted at Apopka, Florida - Rated as % injury

TABLE 10

Comparative evaluations of purple stem color of 6-72-182 and other St. Augustine grasses.

| Selection/Variety | Purple Stem Color[a] Ohio[b] | Florida[c] | California[d] |
|---|---|---|---|
| 6-72-182 | 4.5 | 3 | 0 |
| 6-72-130 | 8.3 | 30 | 4.3 |

TABLE 10-continued

Comparative evaluations of purple stem color of 6-72-182 and other St. Augustine grasses.

| Selection/Variety | Purple Stem Color[a] Ohio[b] | Florida[c] | California[d] |
|---|---|---|---|
| Bitterblue | 8.0 | 10 | — |
| Cal. Common | — | — | 0.7 |
| Delmar | 3.5 | 7 | 0.7 |
| Floratam | 8.3 | 20 | 2.7 |
| Floratine | 8.0 | 8 | — |
| Raleigh | 6.0 | 28 | 1.7 |
| Seville | 4.0 | 0 | — |
| Texas Common | 4.5 | 8 | 1.0 |
| 1081 | 7.5 | 58 | — |
| LSD (.05) | 1.1 | 15 | 0.9 |

[a]Purple stem color rated 1-10, 10 = stolons are very purple, 1 = stolons are entirely green. For Florida, visual estimation of the level of stem purpling in percent.
[b]Test planted in the greenhouse at Marysville, Ohio.
[c]Test planted at Apopka, Florida.
[d]Test planted at South Coast Field Station, University of California - Riverside.

TABLE 11

Comparative ratings of gray leaf spots[a] of 6-72-182 and other St. Augustine grasses at Apopka, Florida.

| Selection/Variety | |
|---|---|
| 6-72-182 | 1.7 |
| 6-72-130 | 1.7 |
| Bittrblue | 3.5 |
| Delmar | 1.0 |
| Floratam | 3.8 |
| Floratine | 2.6 |
| Raleigh | 0.7 |
| Seville | 0.8 |
| Texas Common | 2.4 |
| 1081 | 2.2 |
| LSD (.05) | 0.88 |

[a]Rated 1-10, 10 = most disease.

TABLE 12

Comparative ratings of chinch bug tolerance[a] of 6-72-182 and other St. Augustine grasses.

| Selection/Variety | Florida[b] |
|---|---|
| 6-72-182 | 3.0 |
| 6-72-130 | 1.7 |
| Delmar | 2.0 |
| Bitterblue | 5.0 |
| Floratam | 7.0 |
| Floratine | 2.7 |
| Raleigh | 6.3 |
| Seville | 5.7 |
| Texas Common | 4.7 |

[a]Rated 1-10. 10 = sever damage.
[b]Test planted in the greenhouse at Apopka, Florida.

What is claimed is:

1. A St. Augustine grass, substantially as herein illustrated and described.

* * * * *